(12) United States Patent
Chiu

(10) Patent No.: US 8,080,674 B2
(45) Date of Patent: Dec. 20, 2011

(54) PREPARATION OF POLYMER-FREE R-(+)-α-LIPOIC ACID MAGNESIUM SALT

(75) Inventor: Fang-Ting Chiu, El Dorado Hills, CA (US)

(73) Assignee: Ampac Fine Chemicals LLC., Rancho Cordova, CA (US)

( * ) Notice: Subject to any disclaimer, the term of this patent is extended or adjusted under 35 U.S.C. 154(b) by 313 days.

(21) Appl. No.: 12/483,918

(22) Filed: Jun. 12, 2009

(65) Prior Publication Data

US 2010/0317873 A1 Dec. 16, 2010

(51) Int. Cl.
*C07D 339/00* (2006.01)
*C07D 409/00* (2006.01)
(52) U.S. Cl. .......................................... 549/22; 549/39
(58) Field of Classification Search .................... 549/22, 549/39
See application file for complete search history.

(56) References Cited

U.S. PATENT DOCUMENTS

| | | | |
|---|---|---|---|
| 5,599,835 A | 2/1997 | Fischer | |
| 6,288,106 B1 * | 9/2001 | Pearson et al. | 514/440 |
| 6,479,069 B1 | 11/2002 | Hamilton | |
| 6,585,998 B2 | 7/2003 | Cartwright et al. | |
| 6,864,374 B2 | 3/2005 | Villani et al. | |
| 7,030,154 B2 | 4/2006 | Ames | |
| 2007/0055070 A1 * | 3/2007 | Lawrence et al. | 549/35 |

OTHER PUBLICATIONS

Carlson , R-dihydrolipoic acid (R-DHLA) and Blood Pressure, Web posting, Jun. 25, 2009, http://www.geronova.com/contentJdhla-and-blood-pressureretdved on Jul. 31, 2010.*
Barltrop, J.A. et al.; "The Chemistry of 1,2-Dithiolane (Trimethylene Disulfide) as a Model for the Primary Quantum Conversion Act in Photosynthesis"; 1954, *Chemistry of Trimethylene Disulfide*, vol. 76, pp. 4348-4367.
Carlson, R.; R-dihydrolipoic acid (R-DHLA) and Blood Pressure, Web posting, Jun. 25, 2009, http://www.geronova.com/content/dhla-and-blood-pressuretrived on Jul. 31, 2010.
Dougan, Jennifer A. et al.; "Enhanced oligonucleotide-nanoparticle conjugate stability using thioctic acid modified oligonucleotides"; 2007, *Nucleic Acids Research*, vol. 35, No. 11, pp. 3668-3675.
Endo, Kiyoshi et al.; "Copolymerization of Lipoic Acid with 1,2-Dithiolane and Characterization of the Copolymer as an Interlocked Cyclic Polymer"; 2006, *Macromolecules*, vol. 39, pp. 4038-4043.
Samuel, N.K.P. et al.; "Polymerized-Depolymerized Visicles. Reversible Thiol-Disulfide-Based Phosphatidylcholine Membranes"; 1985, *J. Am. Chem. Soc.*, vol. 107, pp. 42-47.
Suzuki et al.; "Antioxidant Activities of Dihydrolipoic Acid and its Structural Homologues"; 1993, *Free Radical Research*, vol. 18, No. 2, pp. 115-122.
Wagner, Arthur F. et al.; "Properties & Derivatives of α-Lipoic Acid"; 1956 *Merch Sharp & Dohme Research Laboratories*, pp. 5079-5081.

* cited by examiner

*Primary Examiner* — Nizal Chandrakumar
(74) *Attorney, Agent, or Firm* — Kilpatrick Townsend & Stockton LLP.; M. Henry Heines

(57) ABSTRACT

R-α-Lipoic acid and its homologs are converted to their magnesium salts in the presence of a reduced form of the acid, dihydro-(+)-lipoic acid in the case of R-α-lipoic acid itself. The reduced form serves as a polymerization inhibitor, resulting in a Mg di-R-α-lipoate product of higher purity. The reduced acid retained in the product tends to convert to the starting acid, thereby avoiding the inclusion of an extraneous polymerization inhibitor in the product.

10 Claims, No Drawings

PREPARATION OF POLYMER-FREE R-(+)-α-LIPOIC ACID MAGNESIUM SALT

BACKGROUND OF THE INVENTION

α-Lipoic acid, also known as thioctic acid, is an eight-carbon fatty acid with a disulfide linkage joining the carbons 6 and 8 to form a 1,2-dithiolane ring. The acid forms optical isomers of which the isomer R-α-lipoic acid is the most biologically active. R-α-Lipoic acid is an essential nutrient and coenzyme that serves a variety of functions in the treatment and prevention of disease, including liver disease and diabetes. R-α-Lipoic acid is also useful as a nutraceutical, and one OF the recognized nutraceutical forms of the acid is the magnesium salt, magnesium di-R-α-lipoate.

A difficulty encountered in the synthesis of the magnesium salt of R-α-lipoic acid is the susceptibility of lipoic acid to polymerize at the sulfur atoms. The polymerized form is undesirable since it has a lower activity in the human digestive system than the unpolymerized acid or its salts. Polymerization of the acid can be reversed by treatment of the polymer with mercaptoethanol, as described by Barltrop, J. A., et al., "The Chemistry of 1,2-Dithiolane (Trimethylene Disulfide) as a Model for the Primary Quantum Conversion Act in Photosynthesis," *J. Am. Chem. Soc.* 76: 4348-4367 (1954), or by treatment with various reagents including dithiothreitol and Ellman's reagent, as described by Samuel, N. K. P., et al., "Polymerized-Depolymerized Vesicles. Reversible Thiol-Disulfide-Based Phosphatidylcholine Membranes," *J. Am. Chem. Soc.* 107: 42-47 (1985). Polymerization is also recognized as a problem in the conversion of α-lipoic acid to esters, which are disclosed as being useful as prodrugs and as precursors for other lipoic acid derivatives. Lawrence, L. J., et al., in United States Pre-Patent Application Publication US 2007/0055070 A1, propose the addition of L-cysteine as a polymerization inhibitor after the esterification reaction has been performed. A difficulty with all of these methods is that they introduce into the product a foreign species that may have a biological effect other than that sought from the α-lipoic acid, or simply dilute the α-lipoic acid unnecessarily.

SUMMARY OF THE INVENTION

It has now been discovered that polymerization of α-lipoic acid during the conversion of α-lipoic acid or its homologs to the corresponding magnesium salt can be avoided by performing the conversion in the presence of the reduced, i.e., the dihydro-, form of the acid. Thus, for the conversion of R-α-lipoic acid to magnesium di-R-α-lipoate, a small amount of (+)-6,8-dithioloctanoic acid is included in the reaction mixture, and polymerization is at least substantially reduced and in many cases, eliminated entirely. In addition to the unexpected success of this procedure, the reduced form of the acid offers the advantage that it converts to the unreduced acid, i.e., the reactant itself containing the 1,2-dithiolane ring. As a result, a product of high yield and purity is obtained with only the desired activity, and the amount of the reduced form of the acid present in the product will only decrease with time.

These and other features, objects, and advantages of the invention will be more apparent from the description that follows.

DETAILED DESCRIPTION OF THE INVENTION AND PREFERRED EMBODIMENTS

The acids to be converted to magnesium salts by this invention are those having generic formula (I) below:

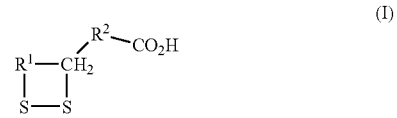

wherein:
$R^1$ is either —$CH_2CH_2$— or —$CH_2CH_2CH_2$—, and
$R^2$ is $C_2$-$C_6$ alkyl.
The preferred $R^1$ is —$CH_2CH_2$—, and a preferred class of $R^2$ is $C_3$-$C_5$ alkyl, with the most preferred $R^2$ being n-butyl. For R-α-lipoic acid, $R^1$ is —$CH_2CH_2$— and $R^2$ is n-butyl.

The magnesium salts produced by the process of the invention are those having the following formula:

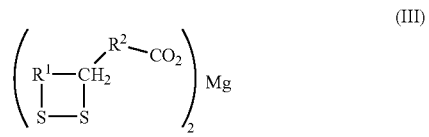

The polymerization inhibitors are represented by the generic formula (II) below:

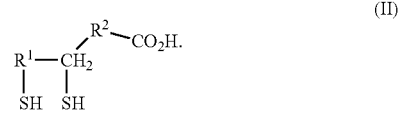

In formulas (III) and (II), $R^1$ and $R^2$ are as defined above for formula (I). While $R^1$ in the starting acid and $R^1$ in the polymerization inhibitor may be the same or different, and likewise $R^2$ in the starting acid and $R^2$ in the polymerization inhibitor may be the same or different, preferred procedures are those in which $R^1$ is the same in both the starting acid and the polymerization, and $R^2$ is likewise the same in both.

The conversion to a magnesium salt can be achieved by conventional methods, and a preferred such method is by reacting the acid with a magnesium alkoxide. Preferred magnesium alkoxides are those in which the alkyl group of the alkoxide moiety is a lower alkyl such as methyl or ethyl, and the most preferred magnesium alkoxide is dimethoxy magnesium, $Mg(OCH_3)_2$.

The term "polymerization-inhibiting" amount is used herein to denote any amount of the reduced acid that will substantially reduce the degree of polymerization of the starting material relative to that which would be obtained with the same starting material under the same conditions. Polymerization is considered to be substantially reduced when the amount of polymer in the product is so low that it is either undetectable or that it does not interfere with the ability of the entire product to be digested in the human digestive system. In most cases, best results will be obtained when the polymerization inhibitor (compound (II)) is present in an amount ranging from about 0.5 to about 25 parts by weight per 100 parts by weight of the starting material (compound (I)), and preferably about 1 to about 10 parts by weight per 100 parts by weight of compound (I). In accordance with the invention, compound (II) is included in the reaction mixture to form the magnesium salt, and the inhibition of polymerization is achieved without adding a further amount of compound (II) to the magnesium salt after the reaction has occurred.

The polymerization inhibitor, shown herein as the reduced form of the starting acid and represented by formula (II), is readily prepared from the starting acid itself by treatment of the acid with a conventional reducing agent. One example is sodium borohydride, $NaBH_4$; other examples will be readily apparent to those of skill in the art.

The reaction conditions to form the magnesium salt can vary widely. One effective means of bringing the reactants into contact is by dissolving them in one or more organic solvents to form a liquid reaction mixture. A preferred class of solvents is alcohol solvents, notably $C_1$-$C_6$ alkyl alcohols. Isopropyl alcohol is an example. The magnesium alkoxide can be separately dissolved in an alcohol solvent prior to its addition to the remaining components of the reaction mixture. The preferred alcohol in which the magnesium alkoxide is dissolved is one with the same alkyl group as that of the magnesium alkoxide. Thus, for $Mg(OCH_3)_2$, the preferred solvent is methyl alcohol.

The reaction is preferably performed at a temperature of 20° C. or below, more preferably at a temperature of less than 18° C., and most preferably at a temperature of from about 10° C. to about 17° C. The reaction can be performed at atmospheric pressure, and is preferably performed under an inert atmosphere, such as nitrogen or argon. Although the ratio of the starting acid to the magnesium alkoxide is not critical to the invention and can vary, the acid is preferably used in a stoichiometric excess relative to the magnesium alkoxide, and the reactants are brought into contact by adding the magnesium alkoxide to the acid gradually over an extended period of time. The reaction can be conducted without the presence of any additional components to the reaction mixture, such as for example the inorganic acid that is a necessary component of the reaction mixture described in the Lawrence et al. patent cited above. The product is a solid at ambient temperature, and can be recovered from the product mixture by conventional solids recovery techniques.

Example 1

A solution of R-α-lipoic acid was prepared by dissolving 10.0 g of R-α-lipoic acid in 300 mL of isopropyl alcohol at 20-25° C. To this solution was added 1.0 g of dihydro-(+)-lipoic acid that had been rinsed with isopropyl alcohol. Following the addition, and while the temperature of the reaction mixture was maintained at 15-20° C., 34 mL of a solution of 8% (by weight) dimethoxy magnesium was added over a six-minute period. The resulting mixture was then stirred at the same temperature for an additional fifteen minutes. The solids were then filtered off, rinsed with isopropyl alcohol, and filtered dry. The solids were then vacuum dried at a temperature of 55° C. or less to yield 10.4 g of product, beige in color, representing a yield of 98.7%, compensating for the dihydro-(+)-lipoic acid present in the product.

The filtration produced a clear filtrate, and the wet cake consisted of fine particles uniform in character. The product was readily soluble at room temperature in a mixture of equal volumes of acetonitrile and water, producing a clear solution with pH 8-9. These characteristics indicated that the product did not contain polymer.

Example 2

The procedure of Example 1 was repeated, using however 150 mL of isopropyl alcohol rather than 300 mL, and 0.55 g of dihydro-(+)-lipoic acid rather than 1.0 g. Similar results were achieved.

Three samples prepared in this manner were compared with a sample of magnesium lipoate prepared by the same procedure except in the absence of the dihydro-(+)-lipoic acid. The samples were then analyzed by differential scanning calorimetry (DSC), and the results are listed in the table below, where the sample prepared in the absence of the dihydro-(+)-lipoic acid is listed as the control.

TABLE

| | Analyses By DSC | | |
|---|---|---|---|
| Sample | Peak 1 Onset Temperature (Energy) | Peak 2 Onset Temperature (Energy) | Peak 3 Onset Temperature (Energy) |
| Control | 180.4° C. (−0.82 W/g) | 202.3° C. (−0.77 W/g) | 279.5° C. (−1.46 W/g) |
| 1 | 195.3° C. (−0.95 W/g) | 222.3° C. (−0.99 W/g) | 278.2° C. (−1.80 W/g) |
| 2 | 204.4° C. (−0.49 W/g) | 221.0° C. (−0.26 W/g) | 290.2° C. (−1.74 W/g) |
| 3 | 206.4° C. (−0.37 W/g) | 223.1° C. (−0.25 W/g) | 286.9° C. (−1.16 W/g) |

The data in the table indicate that the products made in the presence of dihydro-(+)-lipoic acid displayed higher energy, and thus contained less polymeric material.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A process for the formation of a magnesium salt of a cyclic dithio compound of the formula

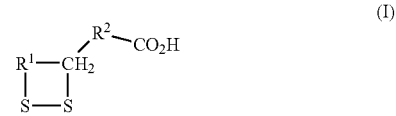

(I)

wherein $R^2$ is $C_2$-$C_6$ alkyl, said process comprising reacting said compound with a magnesium alkoxide in the presence of about 0.5 to about 25 parts by weight of a compound having the formula

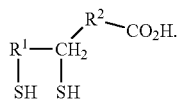

per 100 parts by weight of said cyclic dithio compound.

2. The process of claim 1 wherein $R_2$ is n-butyl.

3. The process of claim 1 wherein said magnesium alkoxide is dimethoxy magnesium.

4. The process of claim 1 wherein $R^2$ is n-butyl, and said magnesium alkoxide is dimethoxy magnesium.

5. The process of claim 1 performed in an alcohol solvent.

6. The process of claim 4 wherein said alcohol solvent is isopropyl alcohol.

7. The process of claim 1 performed in the presence of about 1 to about 10 parts by weight of compound (II) per 100 parts by weight of compound (I).

8. The process of claim 1 performed with compound (I) in stoichiometric excess relative to said magnesium alkoxide.

9. The process of claim 1 performed at a temperature of 20° C. or less.

10. The process of claim 1 performed at a temperature of less than 18° C.

* * * * *